United States Patent
Honold et al.

(10) Patent No.: US 7,550,589 B2
(45) Date of Patent: Jun. 23, 2009

(54) 6-(2-ALKYL-PHENYL)-PYRIDO[2,3-D]PYRIMIDINES USEFUL AS PROTEIN KINASE INHIBITORS

(75) Inventors: Konrad Honold, Penzberg (DE); Wolfgang Schaefer, Mannheim (DE); Stefan Scheiblich, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/660,796

(22) PCT Filed: Sep. 20, 2005

(86) PCT No.: PCT/EP2005/010126
§ 371 (c)(1),
(2), (4) Date: Feb. 21, 2007

(87) PCT Pub. No.: WO2006/032452
PCT Pub. Date: Mar. 30, 2006

(65) Prior Publication Data
US 2007/0259899 A1    Nov. 8, 2007

(30) Foreign Application Priority Data
Sep. 21, 2004  (EP) .................................. 04022372

(51) Int. Cl.
*C07D 471/00* (2006.01)
(52) U.S. Cl. .................. 544/279; 544/117; 548/579
(58) Field of Classification Search ................. 544/279, 544/117; 548/579
See application file for complete search history.

(56) References Cited

FOREIGN PATENT DOCUMENTS

| WO | WO 96/15128 | 5/1996 |
|----|-------------|--------|
| WO | WO 02/090360 | 11/2002 |

OTHER PUBLICATIONS

Patani, et al. Chem. Rev., 96, 1996, pp. 3147-3176.*

* cited by examiner

*Primary Examiner*—James O Wilson
*Assistant Examiner*—Douglas M Willis
(74) *Attorney, Agent, or Firm*—George W. Johnston; Patricia S. Rocha-Tramaloni; Gene J. Yao

(57) ABSTRACT

Objects of the present invention are the compounds of formula (I) their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

2 Claims, No Drawings

6-(2-ALKYL-PHENYL)-PYRIDO[2,3-D]PYRIMIDINES USEFUL AS PROTEIN KINASE INHIBITORS

This application is the national stage of International Application No. PCT/EP2005/010126, filed Sep. 20, 2005, which claims the benefit of European Application No. 04022372.9, filed Sep. 21, 2004, which is hereby incorporated by reference in its entirety.

The present invention relates to novel 6-(2-alkyl-phenyl)-pyrido[2,3-d]pyrimidines, to a process for their manufacture, medicaments containing them and their manufacture as well as the use of these compounds as pharmaceutically active agents.

Some substituted bicyclic nitrogen heterocycles are known in the art for their protein kinase, as well as their tyrosine kinase inhibitory activity. WO 02/090360 discloses pyrido[2,3-d]pyrimidines useful as kinase enzyme inhibitors and for the treatment of hyperproliferative diseases.

WO 03/000011 discloses phosphorus-containing derivatives of pyrido[2,3-d]pyrimidine as protein kinase inhibitors and for the treatment of bone disorders, cancer and signalling disorders in general.

WO 96/15128 discloses 6-aryl-pyrido[2,3-d]pyrimidines as inhibitors of protein tyrosine kinases and for the treatment of atherosclerosis, restenosis, psoriasis, bacterial infections and cancer.

Despite the progress documented in the above-mentioned literature, there remains a need for new compounds with an improved therapeutic index, such as improved activity, tolerability, selectivity or stability to name only a few.

The present derivatives are new compounds of the general formula I

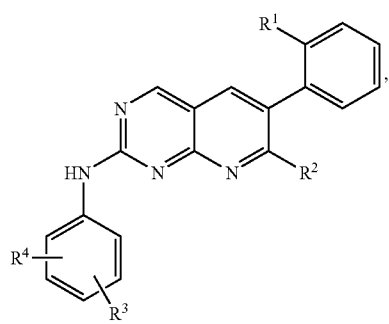

formula I wherein
$R^1$ is —$CH_3$ or —$CF_3$;
$R^2$ is —C(O)—NH-alkyl or —C(O)—N(alkyl)$_2$, all alkyl groups being optionally substituted with
  —OH;
  —NH(alkyl);
  —N(alkyl)$_2$;
  -heterocyclyl; or
  —NH—S(O)$_2$-alkyl;
$R^3$ is heterocyclyl;
  —NH—C(O)-alkyl;
  —NH—S(O)$_2$-alkyl; and
$R^4$ is hydrogen; or alternatively
$R^3$ and $R^4$ are adjacent and together with the phenyl ring to which they are attached form a 4,4-Dioxo-3,4-dihydro-2H-4lambda*6*-benzo[1,4]oxathiin-6-yl moiety;

and pharmaceutically acceptable salts thereof.

The compounds according to this invention show activity as protein kinase inhibitors, in particular src family tyrosine kinase inhibitors, and may therefore be useful for the treatment of diseases mediated by said tyrosine kinases. The family of tyrosine kinases plays an important role in the regulation of cell signaling and cell proliferation by phosphorylating tyrosine residues of peptides and proteins. Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489-495; Biscardi, J. S., et al., Adv. Cancer Res. 76 (2000) 61-119.

Compounds of the present invention may be used as active agents in the prevention and therapy of, for example, transplant rejection, inflammatory bowel syndrome, rheumatoid arthritis, psoriasis, restenosis, allergic asthma, Alzheimer's disease, Parkinson, stroke, osteoporosis, benign hyperplasias and cancer such as colorectal, breast, lung, prostate, pancreatic, gastric, bladder, ovarian, melanoma, neuroblastoma, cervical, kidney or renal cancers, leukemias or lymphomas, or in the manufacture of corresponding medicaments.

The compounds of the present invention have surprisingly been found to show improved metabolic stability and/or selectivity, together with at least the same activity against src-tyrosine kinase compared to compounds known in the art.

Objects of the present invention are the compounds of formula I and pharmaceutically acceptable salts and their enantiomeric forms, the preparation of the above-mentioned compounds, medicaments containing them and their manufacture as well as the use of the above-mentioned compounds in the control or prevention of illnesses, especially of illnesses and disorders as mentioned above or in the manufacture of corresponding medicaments.

As used herein, the term "alkyl" means a saturated, straight-chain or branched-chain hydrocarbon group containing from 1 to 5, preferably from 1 to 3, carbon atoms, such as methyl, ethyl, n-propyl, isopropyl, n-butyl, 2-butyl, t-butyl, n-pentyl, n-hexyl as well as their isomers, preferably methyl or ethyl. "Optionally substituted" alkyl groups are alkyl groups as defined above, which are either unsubstituted or one or, if possible, two times substituted. Preferably such alkyl groups are substituted once.

The term "heterocyclyl" as used herein means a mono- or bicyclic aromatic or non-aromatic ring with 5 to 10 ring atoms, which contains up to 3, preferably 1 or 2 heteroatoms selected independently from N, O or S and the remaining ring atoms being carbon atoms. Said heterocyclyl group is optionally substituted one or several times with alkyl. Preferably said heterocyclyl group is a monocyclic saturated ring with 5 or 6 ring atoms which contains 1 or 2 heteroatoms selected independently from N or O. Said heterocyclyl group can be optionally substituted one or two times by an oxo group or alkyl which is defined as above. Examples of such heterocyclic groups are pyrrolidinyl; methylpyrrolidinyl; imidazolyl; pyrazolyl; 2-methyl-pyrazolyl; dimethyl-pyrazolyl; piperidinyl; methyl-piperidinyl; morpholinyl, preferably pyrrolidinyl and morpholinyl.

Preferably the substituent $R^3$ in formula I is located in para or meta position to —NH—.

An embodiment of the invention are the compounds of formula I, wherein
  $R^2$ is —C(O)—NH-alkyl; said alkyl group is optionally substituted once with
    —NH(alkyl);
    -pyrrolidinyl; or
    —NH—S(O)$_2$-alkyl;

$R^3$ is morpholino;
—NH—S(O)$_2$-alkyl; or
—NH—C(O)-alkyl; and
$R^4$ is hydrogen; or alternatively
$R^3$ and $R^4$ are adjacent and together with the phenyl ring to which they are attached form a 4,4-Dioxo-3,4-dihydro-2H-4lambda*6*-benzo[1,4]oxathiin-6-yl moiety.

An embodiment of the invention are the compounds of formula I, wherein
$R^2$ is —C(O)—NH-ethylene-NH-alkyl, —C(O)—NH-methylene-pyrrolidinyl; —C(O)—NH-ethylene-pyrrolidinyl or —C(O)—NH-ethylene-NH—S(O)$_2$-alkyl;
$R^3$ is morpholino;
—NH—S(O)$_2$-alkyl; or
—NH—C(O)-alkyl; and
$R^4$ is hydrogen; or alternatively
$R^3$ and $R^4$ are adjacent and together with the phenyl ring to which they are attached form a 4,4-Dioxo-3,4-dihydro-2H-4lambda*6*-benzo[1,4]oxathiin-6-yl moiety.

Another embodiment of the invention are the compounds of formula I, wherein
$R^1$ is —CH$_3$.

Still another embodiment of the invention are the compounds of formula I, wherein
$R^1$ is —CH$_3$;
$R^2$ is —C(O)—NH-alkyl; said alkyl group is optionally substituted once with
—NH(alkyl);
-pyrrolidinyl; or
—NH—S(O)$_2$-alkyl;
$R^3$ is morpholino;
—NH—S(O)$_2$-alkyl; or
—NH—C(O)-alkyl; and
$R^4$ is hydrogen; or alternatively
$R^3$ and $R^4$ are adjacent and together with the phenyl ring to which they are attached form a 4,4-Dioxo-3,4-dihydro-2H-4lambda*6*-benzo[1,4]oxathiin-6-yl moiety.

Another embodiment of the invention are the compounds of formula I, wherein
$R^1$ is —CH$_3$;
$R^2$ is —C(O)—NH-ethylene-NH-alkyl, —C(O)—NH-methylene-pyrrolidinyl; —C(O)—NH-ethylene-pyrrolidinyl or —C(O)—NH-ethylene-NH—S(O)$_2$-alkyl;
$R^3$ is morpholino;
—NH—S(O)$_2$-alkyl; or
—NH—C(O)-alkyl; and
$R^4$ is hydrogen.

Still another embodiment of the invention are the compounds of formula I, wherein
$R^1$ is —CH$_3$; and
$R^2$ is —C(O)—NH-ethylene-NH—CH$_3$.

Still another embodiment of the invention are the compounds of formula I, wherein
$R^1$ is —CH$_3$;
$R^2$ is —C(O)—NH-ethylene-NH—CH$_3$;
$R^3$ is morpholino;
—NH—S(O)$_2$-alkyl; or
—NH—C(O)-alkyl; and
$R^4$ is hydrogen.

Such compounds are for example:
2-(3-Acetylamino-phenylamino)-6-o-tolyl-pyrido[2,3-d]pyrimidine-7-carboxylic acid (2-methylamino-ethyl)-amide;
2-(3-Methanesulfonylamino-phenylamino)-6-o-tolyl-pyrido[2,3-d]pyrimidine-7-carboxylic acid (2-methylamino-ethyl)-amide; and
2-(4-Morpholin-4-yl-phenylamino)-6-o-tolyl-pyrido[2,3-d]pyrimidine-7-carboxylic acid (2-methylamino-ethyl)-amide.

Still another embodiment of the invention are the compounds of formula I, wherein
$R^1$ is —CH$_3$; and
$R^2$ is —C(O)—NH-methylene-pyrrolidinyl.

Still another embodiment of the invention are the compounds of formula I, wherein
$R^1$ is —CH$_3$;
$R^2$ is —C(O)—NH-methylene-pyrrolidinyl;
$R^3$ is morpholino;
—NH—S(O)$_2$-alkyl; or
—NH—C(O)-alkyl; and
$R^4$ is hydrogen.

Such compounds are for example:
2-(3-Acetylamino-phenylamino)-6-o-tolyl-pyrido[2,3-d]pyrimidine-7-carboxylic acid (pyrrolidin-2-ylmethyl)-amide;
2-(3-Methanesulfonylamino-phenylamino)-6-o-tolyl-pyrido[2,3-d]pyrimidine-7-carboxylic acid (pyrrolidin-2-ylmethyl)-amide; and
2-(4-Morpholin-4-yl-phenylamino)-6-o-tolyl-pyrido[2,3-d]pyrimidine-7-carboxylic acid (pyrrolidin-2-ylmethyl)-amide.

Still another embodiment of the invention are the compounds of formula I, wherein
$R^1$ is —CH$_3$; and
$R^2$ is —C(O)—NH-ethylene-NH—S(O)$_2$-alkyl.

Still another embodiment of the invention are the compounds of formula I, wherein
$R^1$ is —CH$_3$;
$R^2$ is —C(O)—NH-ethylene-NH—S(O)$_2$-alkyl;
$R^3$ is morpholino;
—NH—S(O)$_2$-alkyl; or
—NH—C(O)-alkyl; and
$R^4$ is hydrogen.

Such compounds are for example:
2-(3-Acetylamino-phenylamino)-6-o-tolyl-pyrido[2,3-d]pyrimidine-7-carboxylic acid (2-methanesulfonylamino-ethyl)-amide;
2-(3-Methanesulfonylamino-phenylamino)-6-o-tolyl-pyrido[2,3-d]pyrimidine-7-carboxylic acid (2-methanesulfonylamino-ethyl)-amide; and
2-(4-Morpholin-4-yl-phenylamino)-6-o-tolyl-pyrido[2,3-d]pyrimidine-7-carboxylic acid (2-methanesulfonylamino-ethyl)-amide.

Another embodiment of the invention are the compounds of formula I, wherein
$R^1$ is —CF$_3$.

Still another embodiment of the invention are the compounds of formula I, wherein
$R^1$ is —CF$_3$;
$R^2$ is —C(O)—NH-alkyl; said alkyl group is optionally substituted once with
—NH(alkyl);
-pyrrolidinyl; or
—NH—S(O)$_2$-alkyl;
$R^3$ is morpholino;
—NH—S(O)$_2$-alkyl; or
—NH—C(O)-alkyl; and
$R^4$ is hydrogen; or alternatively
$R^3$ and $R^4$ are adjacent and together with the phenyl ring to which they are attached form a 4,4-Dioxo-3,4-dihydro-2H-4lambda*6*-benzo[1,4]oxathiin-6-yl moiety.

Still another embodiment of the invention are the compounds of formula I, wherein $R^1$ is —$CF_3$;

$R^2$ is —C(O)—NH-ethylene-NH-alkyl, —C(O)—NH-methylene-pyrrolidinyl; —C(O)—NH-ethylene-pyrrolidinyl or —C(O)—NH-ethylene-NH—S(O)$_2$-alkyl;

$R^3$ is morpholino;
  —NH—S(O)$_2$-alkyl; or
  —NH—C(O)-alkyl; and $R^4$ is hydrogen; or alternatively $R^3$ and $R^4$ are adjacent and together with the phenyl ring to which they are attached form a 4,4-Dioxo-3,4-dihydro-2H-4lambda*6*-benzo[1,4]oxathiin-6-yl moiety.

Still another embodiment of the invention are the compounds of formula I, wherein $R^1$ is —$CF_3$; and $R^2$ is —C(O)—NH-methylene-pyrrolidinyl.

Still another embodiment of the invention are the compounds of formula I, wherein $R^1$ is —$CF_3$;

$R^2$ is —C(O)—NH-methylene-pyrrolidinyl;

$R^3$ is morpholino;
  —NH—S(O)$_2$-alkyl; or
  —NH—C(O)-alkyl; and $R^4$ is hydrogen; or alternatively $R^3$ and $R^4$ are adjacent and together with the phenyl ring to which they are attached form a 4,4-Dioxo-3,4-dihydro-2H-4lambda*6*-benzo[1,4]oxathiin-6-yl moiety.

Such compounds are for example:

2-(4-Morpholin-4-yl-phenylamino)-6-(2-trifluoromethyl-phenyl)-pyrido[2,3-d]pyrimidine-7-carboxylic acid (pyrrolidin-2-ylmethyl)-amide;

2-(3-Acetylamino-phenylamino)-6-(2-trifluoromethyl-phenyl)-pyrido[2,3-d]pyrimidine-7-carboxylic acid (pyrrolidin-2-ylmethyl)-amide;

2-(3-Methanesulfonylamino-phenylamino)-6-(2-trifluoromethyl-phenyl)-pyrido[2,3-d]pyrimidine-7-carboxylic acid (pyrrolidin-2-ylmethyl)-amide; and 2-(4,4-Dioxo-3,4-dihydro-2H-4lambda*6*-benzo[1,4]oxathiin-6-ylamino)-6-(2-trifluoromethyl-phenyl)-pyrido[2,3-d]pyrimidine-7-carboxylic acid (pyrrolidin-2-ylmethyl)-amide.

Still another embodiment of the invention are the compounds of formula I, wherein $R^1$ is —$CF_3$; and $R^2$ is —C(O)—NH-ethylene-NH—S(O)$_2$-alkyl.

Still another embodiment of the invention are the compounds of formula I, wherein $R^1$ is —$CF_3$;

$R^2$ is —C(O)—NH-ethylene-NH—S(O)$_2$-alkyl;

$R^3$ is morpholino;
  —NH—S(O)$_2$-alkyl; or
  —NH—C(O)-alkyl; and $R^4$ is hydrogen; or alternatively $R^3$ and $R^4$ are adjacent and together with the phenyl ring to which they are attached form a 4,4-Dioxo-3,4-dihydro-2H-4lambda*6*-benzo[1,4]oxathiin-6-yl moiety.

Such compounds are for example:

2-(4-Morpholin-4-yl-phenylamino)-6-(2-trifluoromethyl-phenyl)-pyrido[2,3-d]pyrimidine-7-carboxylic acid (2-methanesulfonylamino-ethyl)-amide;

2-(3-Acetylamino-phenylamino)-6-(2-trifluoromethyl-phenyl)-pyrido[2,3-d]pyrimidine-7-carboxylic acid (2-methanesulfonylamino-ethyl)-amide;

2-(3-Methanesulfonylamino-phenylamino)-6-(2-trifluoromethyl-phenyl)-pyrido[2,3-d]pyrimidine-7-carboxylic acid (2-methanesulfonylamino-ethyl)-amide; and 2-(4,4-Dioxo-3,4-dihydro-2H-4lambda*6*-benzo[1,4]oxathiin-6-ylamino)-6-(2-trifluoromethyl-phenyl)-pyrido[2,3-d]pyrimidine-7-carboxylic acid (2-methanesulfonylamino-ethyl)-amide.

Another embodiment of the invention is a process for the manufacture of the compounds according to this invention, wherein a) the carboxylate group in the compounds of formula (III)

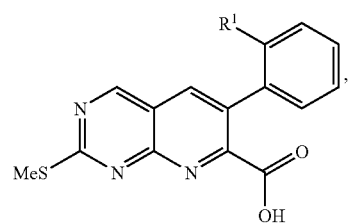

formula (III)

wherein $R^1$ has the significance given above for formula (I), is converted into an amide derivative of formula (IV)

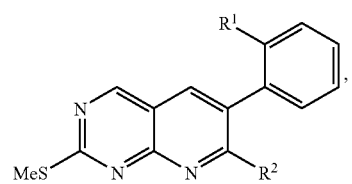

formula (IV)

wherein $R^1$ and $R^2$ have the significance given above for formula (I);

b) the sulfanyl group in the compounds of formula (IV) is converted to the corresponding sulfoxide group, which sulfoxide group is c) substituted by the respective anilines of formula (VI)

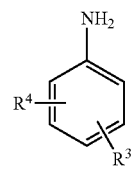

formula (VI)

wherein $R^3$ and $R^4$ have the significance given above for formula (I), to give the compounds of the general formula (I);

d) if desired said compound of the general formula (I), obtained from (c), is converted into a pharmaceutically acceptable salt.

The derivatives of the general formula (I) or a pharmaceutically acceptable salt thereof, may be prepared by any process known to be applicable for the preparation of chemically-related compounds by the one skilled in the art. Such processes, when used to prepare the derivatives of formula (I), or a pharmaceutically-acceptable salt thereof, are provided as a further feature of the invention and are illustrated by the following representative examples of scheme 1, in which, unless otherwise stated $R^1$, $R^2$, $R^3$ and $R^4$ have the significance given herein before. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

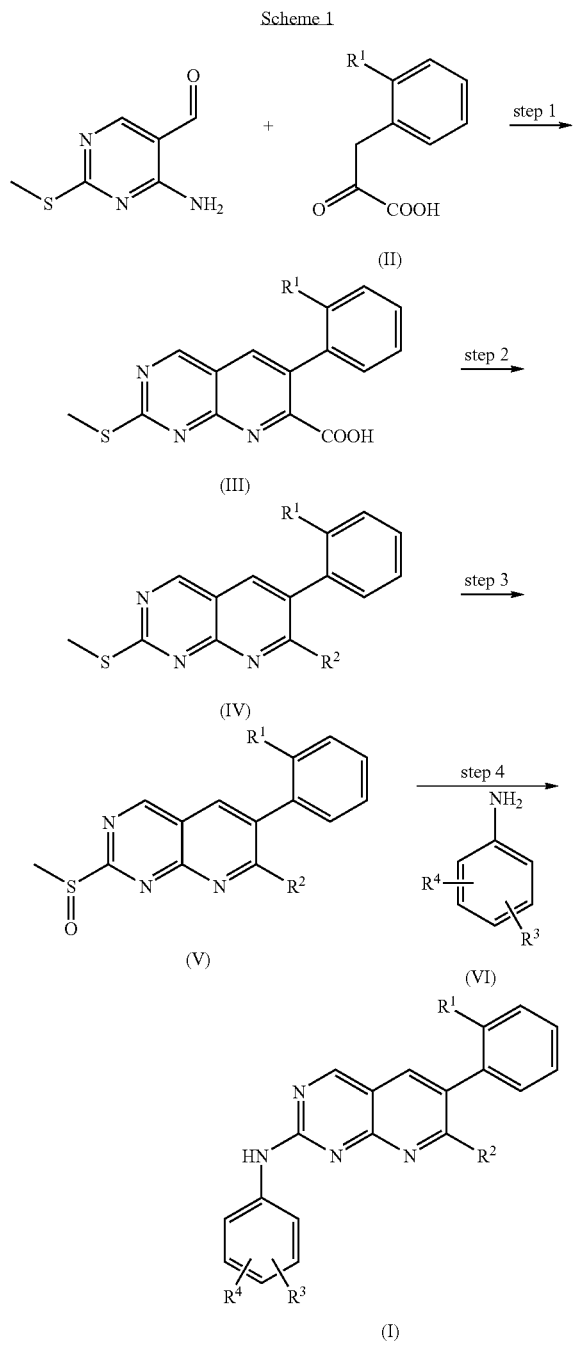

Scheme 1

Step 1:
Substituted arylpyruvic acids of formula (II) can be condensed with 4-Amino-2-methylsulfanylpyrimidine-5-carbaldehyde to give the compounds of formula (III). Said condensation reaction can be performed under basic conditions, e.g. with sodium hydroxide (NaOH) in water or methanol (MeOH) or 1,8-Diazabicyclo[5.4.0]undec-7-ene (DBU) or potassium tert-butoxylate (KOtBu) in dimethyl formamide (DMF), 1-Methyl-2-pyrrolidinone (NMP) or tetrahydrofuran (THF). Alternatively, the condensation reaction is performed in acetic acid in the presence of sodium acetate. Reaction temperatures range from room temperature (RT) to 150° C.

Step 2:
The appropriate carboxylic acids of formula (III) can be converted into the amide derivatives of formula (IV) by standard procedures known in the art. For instance, the acid is first activated by reaction with a carbodiimide or carbonyl diimidazole or oxalyl chloride, and subsequently reacted without isolation with the appropriate substituted amine. This reaction is best performed in an inert solvent like THF, $CH_2Cl_2$ or NMP at temperatures ranging from 0° C. to 150° C.

Step 3:
A methylthio or alternatively any other alkylthio or arylthio group on position 2 of the pyridopyrimidines of formulae (IV) can be converted into a suitable leaving group by oxidation to the corresponding sulfoxide of formula (V), or the corresponding sulfone. Suitable reagents are for instance 3-Chloroperoxybenzoic acid (mCPBA) or 2-benzenesulfonyl-3-phenyl-oxaziridine in inert solvents like dichlormethane ($CH_2Cl_2$), chloroform ($CHCl_3$), or methyl tert-butyl ether (MTBE) at temperatures ranging from −40° C. to +65° C.

Step 4:
The sulfoxides or sulfones from step 3 can be reacted in purified form or as crude products with the anilines of formula (VI) to give 2-anilino substituted pyridopyrimidines of formula (I). The reaction may be performed in excess aniline as the solvent or in an inert solvent like $CH_2Cl_2$, toluene, acetonitrile, DMF, dimethyl sulfoxide (DMSO) or NMP, and at temperatures in the range from 0° C. to 150° C. Acids like trifluoroacetic acid (TFA) or hydrochloric acid (HCl) may be added to catalyze the reaction. If mCPBA has been used for the previous oxidation step, the formed m-chlorobenzoic acid present in the crude reaction mixture may serve as the catalyst.

During this reaction sequence some functional groups on the substituents $R^2$ may require the use of an appropriate protecting group known to those skilled in the art, which can be cleaved off at the end of the described reaction sequence. Examples for such protecting groups are tert.-butyloxycarbonyl or benzyloxycarbonyl for the protection of secondary or primary amine functionalities.

The compounds of the general formula (I) can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, furnaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Stahl, P. H., and Wermuth, G., (editors), Handbook of Pharmaceutical Salts, Verlag Helvetica Chimica Acta (VHCA), Zürich (2002) or Bastin, R. J., et al., Organic Proc. Res. Dev. 4 (2000) 427-435.

The compounds according to this invention and their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

An embodiment of the invention is a medicament containing one or more compounds according to formula (I) as active ingredients together with pharmaceutically acceptable adjuvants.

Another embodiment of the invention is said medicament for the treatment of diseases mediated by an inappropriate activation of src family tyrosine kinases.

Another embodiment of the invention is said medicament for the treatment of inflammatory-, immunological-, CNS disorders or bone diseases Another embodiment of the invention is said medicament for the treatment of cancer.

Another embodiment of the invention is the use of one or more compounds according to formula (I) for the manufacture of medicaments for the treatment of diseases mediated by an inappropriate activation of src family tyrosine kinases.

Another embodiment of the invention is the use of one or more compounds according to formula (I) as src family tyrosine kinase inhibitors.

Another embodiment of the invention is the use of one or more compounds according to formula (I) as cell signaling-regulating and anti-proliferating agents.

Another embodiment of the invention is the use of one or more compounds according to formula (I) for the treatment of inflammatory-, immunological-, CNS disorders or bone diseases.

Another embodiment of the invention is the use of one or more compounds of formula I according to formula (I) for the treatment of cancer.

A pharmaceutical preparation was obtained e.g. by using the following procedure:

1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads:gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 µm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I with particle sizes between 1 and 10 µm. The suspensions are suitable for oral applications and were used in the in vivo pharmacokinetic testings described below.

Pharmacological Activity:

The activity of the compounds according to this invention as inhibitors for the src-family tyrosine kinases was shown by using the following assay.

SRC-Inhibitor-Assay Parameters:

Reaction Mixture:

| | |
|---|---|
| ATP | 5 µM |
| Peptide (Ro + Ja133-Ro): | 10 µM |
| Ja133-Ro | 196 nM |
| Ro | 9.8 µM |
| PT66 | 230 ng/ml |
| Assay buffer: | 4 mM MgCl2 |
| | 2 mM TCEP |
| | 50 mM HEPES |
| | 0.1% Tween 20 |
| | pH 7.3 |
| Enzyme: | 2.5 U/ml |
| Inhibitor: | max. 25 µM |
| | min. 0.42 nM |
| Material: | |

Eu-labelled Phosphotyrosine Antibody: for Lck Cisbio Mab PT66-K, for Src EG&G Wallac PT66 Eu-W1024 (all commercially available).

Peptides: Ro: $NH_2$-A-E-E-E-I-Y-G-E-F-E-A-K-K-K-K-$CONH_2$, and

Ja133-Ro: Ja133-G-Aminocaprylic acid-A-E-E-E-I-Y-G-E-F-E-A-K-K-K-K-$CONH_2$, wherein Ja133 is Light-Cycler-Red 640-N-hydroxy succinimide ester;

whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 µmol scale) of a Rink-Linker modified polystyrene solid phase by repeatedly conjugating an twenty fold excess of amino acids each protected by temporary piperidine labile Fmoc- and permanent acid labile tert-Bu—, BOC- and O-tert-Bu-groups depending on the side chain function. The substrate sequence AEEEIYGEFEAKKKK was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased from Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoroacetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0].

Enzymes: Upstate Lck (p56$^{lck}$, active), Upstate Src (p60$^{c\text{-}src}$, partially purified) were purchased from UBI, Upstate Biotech, Inc.

Time-resolved Fluorescence Assay: Reader: Perkin Elmer, Wallac Viktor 1420-040 multilabel counter; Liquid handling system: Beckman Coulter, Biomek 2000.

ATP, Tween™ 20, 4-(2-hydroxyethyl)-1-piperazineethanesulfonic acid (HEPES) were purchased from Roche Molecular Biochemicals, $MgCl_2$ and $MnCl_2$ were purchased from Merck Eurolab, Tris(2-carboxyethyl)phosphine hydrochloride (TCEP) was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (XLfit software (ID Business Solution Ltd., Guilford, Surrey, UK))

| Example-No. | IC50 src [µM] | IC50 lck [µM] |
|---|---|---|
| 1 | 0.0007 | 0.008 |
| 3 | 0.001 | 0.0118 |
| 5, 7, 8, 9, 11, 14, 15 | 0.0005-0.005 | 0.001-0.020 |
| 2, 17 | 0.005-0.050 | 0.020-0.050 |

In vivo assay on tumor inhibition:

To generate primary tumors, HT-29 colon carcinoma cells (ATTC HTB-38) ($2.5 \times 10^6$ in a volume of 100 µl) are injected subcutaneously into the left flank of female SCID mice (SCID beige (Severe Combined Immunodeficient/beige mice available from Charles River, Sulzfeld, Germany)) using a 1 ml syringe and a 26G needle. The HT-29 cells have been originally obtained from the NCI and deposited in a working cell bank. The cells are thawed and expanded in vitro before use in the experiment. Mice are assigned to the treatment groups on day 9. For grouping (n=12 mice per group), the animals are randomized to get a similar mean primary tumor volume of ca. 120 mm³ per group. The test compounds are administered orally once per day as a suspension in 7.5% gelatine 0.22% NaCl with an administration volume of 10 ml/kg based on actual body weights. Treatment is initiated on day 10, and carried out until day 30, the final day of the study. The subcutaneous primary tumors are measured twice weeldy, starting on day 7 after tumor cell implantation, in two dimensions (length and width) using an electronic caliper. The volume of the primary tumor is calculated using the formula: $V[mm^3]=(length[mm] \times width[mm] \times width[mm])/2$. In addition, the body weight of all animals is recorded at least twice weekly. Finally, at the end of the study the tumors are explanted and weighed.

The following examples and references are provided to aid the understanding of the present invention, the true scope of which is set forth in the appended claims. It is understood that modifications can be made in the procedures set forth without departing from the spirit of the invention.

EXAMPLES

Starting Materials a) 3-(2-Methylphenyl)-2-oxopropionic acid 11 g 2-Acetylamino-3-(2-methyl-phenyl)-acrylic acid in 150 ml 5M aqueous HCl were refluxed for 2.5 hrs. After addition of 400 ml of ice water the resulting suspension was extracted several times with dichloromethane. The organic phases were washed three times with concentrated sodium carbonate solution, the aqueous phases acidified to pH 1 with HCl and again extracted with dichloromethane. The solvent was evaporated and the residues crystallized upon standing over night at room temperature. It was dissolved in dichloromethane, filtered, and again evaporated at 60° C. The warm residue was treated with acetonitrile and cooled to yield a white precipitate. Recrystallisation from dichloromethane/hexanes/acetonitrile (6:2:2) gave 4.2 g of the title product.

b) 2-Methylsulfanyl-6-o-tolyl-pyrido[2,3-d]pyrimidine-7-carboxylic acid 1.05 g of the product from example a) were dissolved in 11 ml dry dimethylformamide (DMF) and cooled to 0° C. 2.00 g 1,8-diaza-7-bicyclo[5.4.0]undecene (DBU) were added dropwise and 5 min later 1.00 g 4-amino-2-methylsulfanylpyrimidine-5-carbaldehyde were added. The mixture was heated to 85° C. for 6 hrs. Another 0.2 g of ketoacid a) were added and stirring continued for 12 hrs. The mixture was cooled, DMF removed under vacuum and the residue dissolved in 150 ml water. After acidifying to pH 2 with HCl the crude product precipitated and was isolated by filtration. The filtrate was extracted with dichloromethane, solvent evaporated and the residue combined with the crude product. Recrystallisation from dichloromethane/ether yielded 1.5 g of the title product.

c) 2-Methylsulfanyl-6-o-tolyl-pyrido[2,3-d]pyrimidine-7-carboxylic acid (2-methanesulfonylaminoethyl)-amide 0.50 g of intermediate from example b) were dissolved in 2 ml dry dimethylformamide (DMF) and treated with 0.221 g carbonyl diimidazole at room temperature. After 1 hrs 0.159 g N-(2-Amino-ethyl)-methanesulfonamide were added to the mixture and stirring continued for 2 hrs. 200 ml brine were added and a first crop of crude product isolated by filtration.

The filtrate was extracted with dichloromethane, the organic phase evaporated and the residue combined with the crude product. Chromatography on silica with ethyl acetate/hexanes yielded 120 mg of the title product.

d) (R)-2-{[(2-Methylsulfanyl-6-o-tolyl-pyrido[2,3-d]pyrimidine-7-carbonyl)-amino]-methyl}-pyrrolidine-1-carboxylic acid tert-butyl ester Analogous to example c) using 0.258 g of (R)-2-aminomethyl-pyrrolidine-1-carboxylic acid tert-butyl ester (purchased from AstaTech)

Yield 208 mg e) 2-Methyl-4-(2-trifluoromethyl-benzylidene)-4H-oxazol-5-one 20 g o-Trifluoromethyl benzaldehyde, 60 g N-acetylglycine and 12 g sodium acetate were stirred in 68.2 g acetic anhydride at 80° C. for 22 hrs. The mixture was poured into 100 ml ice water, the precipitate filtered off and washed with water. Yield 35 g of wet crude product, used without further purification fort the next step.

f) 2-Acetylamino-3-(2-trifluoromethyl-phenyl)-acrylic acid

The product from example e) was stirred in 2 M aqueous sodium hydroxide at 60° C. for 1 hr. After cooling to room temperature 2.5 g active charcoal were added and the mixture was stirred for 20 min, then filtered. The filtrate was acidified to pH 1-2 by addition of conc. HCl. The resulting precipitate was isolated by filtration, washed with water and dried under vacuum to yield 24.8 g of the title product.

g) 2-Oxo-3-(2-trifluoromethylphenyl)-propionic acid 24 g of the product of ex. f) were suspended in 175 ml 5M HCl and stirred at 100° C. for 5 hrs. After cooling to room temperature, precipitated product was isolated by filtration (2.05 g). From the filtrate an oily phase was separated which solidified on standing to yield another 15.8 g of the title product.

h) 2-Methylsulfanyl-6-(2-trifluoromethyl-phenyl)-pyrido[2,3-d]pyrimidine-7-carboxylic acid 3.2 g of the product from ex. g) in 20 ml dry dimethylformamide (DMF) at 0-5° C. were treated with 4.28 g 1,8-diaza-7-bicyclo[5.4.0]undecene (DBU) for 5 min. 2.05 g 4-amino-2-methylsulfanylpyrimidine-5-carbaldehyde were added and the mixture was heated to 70-80° C. for 6 hrs. Stirring was continued at room temperature for another 16 hrs, then the DMF was evaporated under vacuum. The residue was taken up in 70 ml concentrated sodium carbonate solution and 40 ml ethyl acetate. The organic phase was removed and the carbonate phase was washed with ethyl acetate. The pH was adjusted to 1-2 by addition of conc. HCl, and the product extracted with ethyl acetate. Evaporation of the solvent gave 1.1 g a of a solid residue which was further purified by boiling up in a small amount of ethyl acetate and filtering.

Yield 1.02 g of the title product.

i) 2-Methylsulfanyl-6-(2-trifluoromethylphenyl)-pyrido[2,3-d]pyrimidine-7-carboxylic acid (2-methanesulfonylamino-ethyl)-amide 0.5 g of the intermediate from ex. h) I 8 ml dry dimethylformamide (DMF) were treated with 0.275 g carbonyl diimidazole at room temperature for 1 hr. 0.283 g N-(2-Amino-ethyl)-methanesulfonamide in 2 ml DMF were added to the mixture and stirring continued for 1 hr. The solvent was removed under vacuum and the residue purified by chromatography on silica and ethyl acetate/hexanes eluent.

Yield 0.495 g of the title product.

Final Products

Example 1

(R)-2-(3-Acetylamino-phenylamino)-6-o-tolyl-pyrido[2,3-d]pyrimidine-7-carboxylic acid (pyrrolidin-2-ylmethyl)-amide 70 mg of the intermediate from example d) in 0.5 ml dichloromethane were treated dropwise with a dried (sodium sulfate) solution of 1.1 equivalents meta-chloroperbenzoic acid (mCPBA) in dichloromethane at 0-5° C. The oxidation was monitored by HPLC, and after 30 min another 0.1 equivalents of mCPBA were added. After completion of the oxidation, excess peracid was quenched by the addition of a few drops of dimethylsulfane and stirring for 10 min at room temperature. 25 mg (1.1 equivalents) of 3-acetamino-anilin in 0.5 ml dichloromethane were added to the mixture and stirring was continued for 16 hrs at room temperature.

Chromatography on silica using a gradient from dichloromethane to dichloromethane/methanol 830:1) yielded the Boc-protected title product. Cleavage of the protection group was achieved by stirring in a mixture of 1 ml dichloromethane and 1 ml 1M HCl in ether at room temperature for 3 hrs. The mixture was diluted with 15 ml dichloromethane, washed with conc. sodium bicarbonate solution and evaporated. The crude title product was further purified by crystallisation from ethyl acetate/ether.

Yield 26 mg $^1$H-NMR (400 MHz, CDCl3): 9.22 (br s, 1H); 9.03 (s, 1H); 8.57 (br s, 1H); 8.17 (br s, 1H); 8.00 (br s, 1H); 7.86 (s, 1H); 7.73 (d, 1H); 7.29-7.10 (m, 4H); 7.05 (br s, 1H); 6.85 (d, 1H); 3.60-3.45 (m, 1H); 3.30-3.13 (m, 1H); 3.10-2.95 (m, 1H); 2.94-2.82 (m, 1H); 2.82-2.72 (m, 1H); 2.06 (s, 3H); 2.00 (s, 3H); 1.87-1.52 (m, 3H); 1.35-1.20 (m, 1H).

Example 2

2-(4,4-Dioxo-3,4-dihydro-2H-4lambda*6*-benzo[1,4]oxathiin-6-ylamino)-6-(2-trifluoromethyl-phenyl)-pyrido[2,3-d]pyrimidine-7-carboxylic acid (2-methanesulfonylamino-ethyl)-amide A dried (sodium sulfate) solution of 45 mg mCPBA in 3 ml dichloromethane was added dropwise at room temperature to 80 mg of intermediate i) in 2 ml dichloromethane. After 30 min 65.6 mg of 4,4-dioxo-3,4-dihydro-2H-4lambda*6*-benzo[1,4]oxathiin-6-ylamine (prepared as described in WO 04/41823) were added and stirring was continued for 16 hrs. The mixture was washed with 10% aqueous acetic acid, and the organic phase was dried, evaporated and chromatographed on silica/ethyl acetate. The obtained crude product was recrystallized from ethyl acetate/hexanes to yield 75 mg of the title product.

¹H-NMR (400 MHz, DMSO-d6): 10.52 (s, 1H); 9.49 (s, 1H); 8.89 (br t, 1H); 8.35 (s, 1H); 8.28 (br s, 2H); 7.81 (d, 1H); 7.70 (t, 1H); 7.62 (t, 1H); 7.43 (d, 1H); 7.17 (d, 1H); 7.08 (br t, 1H); 4.77 (br s, 1H); 3.87 (br s, 2H); 3.35-3.15 (m, 2H); 3.05-2.95 (m, 2H); 2.90 (s, 3H).

The following examples were prepared in analogous procedures as for example 1 or example 2, using or preparing the appropriate starting materials.

| Example-No. | Systematic Name | ¹H-NMR |
|---|---|---|
| 3 | 2-(3-Acetylamino-phenylamino)-6-o-tolyl-pyrido[2,3-d]pyrimidine-7-carboxylic acid (2-methanesulfonylamino-ethyl)-amide | (400MHz, CDCl3): 9.18(s, 1H); 8.38(br m, 2H); 8.03(s and br s, together 2H); 7.47(d, 1H); 7.40-7.21(m, 6H); 7.15(d, 1H)5.62(br s, 1H); 3.52(m, 2H)3.33(m, 2H); 2.95(s, 3H), 2.19(s, 3H); 2.12(s, 3H); |
| 4 | 2-(3-Methanesulfonylamino-phenylamino)-6-o-tolyl-pyrido[2,3-d]pyrimidine-7-carboxylic acid (2-methanesulfonylamino-ethyl)-amide | (400MHz, CDCl3): 9.21(s, 1H); 8.45(br m, 2H); 8.04(s, 1H); 7.71(br s, 1H); 7.36-7.21(m, 6H); 7.13(m, 2H)5.41(br s, 1H); 3.54(m, 2H)3.39(m, 2H); 3.08(s, 3H), 3.04(s, 3H); 2.11(s, 3H); |
| 5 | 2-(4-Morpholin-4-yl-phenylamino)-6-o-tolyl-pyrido[2,3-d]pyrimidine-7-carboxylic acid (2-methanesulfonylamino-ethyl)-amide | (400MHz, CDCl3): 9.12(s, 1H); 8.45(br t, 1H); 7.95(s, 1H); 7.77 and 7.70(2x br s, together 3H); 7.40-7.21(m, 3H); 7.15(d, 1H); 7.02(d, 2H); 5.42(br s, 1H); 3.92(t, 4H)3.57(m, 2H); 3.36(m, 2H); 3.20(t, 4H); 2.93(s, 3H), 2.10(s, 3H); |
| 6 | (R)-2-(3-Methanesulfonylamino-phenylamino)-6-o-tolyl-pyrido[2,3-d]pyrimidine-7-carboxylic acid (pyrrolidin-2-ylmethyl)-amide | (400MHz, CDCl3): 9.01(s, 1H); 8.49 and 8.42(2x br s, together 2H); 8.10(br s, 1H); 7.83(s, 1H); 7.25-6.98(m, 7H); 6.89(d, 1H); 3.60-3.45(m, 1H); 3.35-3.25(m, 1H); 3.25-3.05(m, 1H); 3.03-2.95(m, 1H); 2.95-2.82(m) and 2.90(s, together 4H); 1.98(s, 3H); 1.87-1.52(m, 3H); 1.35-1.20(m, 1H); |
| 7 | (R)-2-(4-Morpholin-4-yl-phenylamino)-6-o-tolyl-pyrido[2,3-d]pyrimidine-7-carboxylic acid (pyrrolidin-2-ylmethyl)-amide | (400MHz, CDCl3): 9.11(s, 1H); 8.38(br s, 1H); 8.13(br s, 1H); 7.90(s, 1H); 7.69(br s, 2H); 7.35-7.19(m, 3H); 7.20-7.10(m, 1H); 6.97(d, 2H); 3.89(t, 4H); 3.57-3.44(m, 1H); 3.38-3.25(m, 1H); 3.25-3.05(m) and 3.16(t, together 4H); 2.98-2.82(m, 2H); 2.09(s, 3H); 1.91-1.57(m, 3H); 1.43-1.26(m, 1H); |
| 8 | 2-(3-Acetylamino-phenylamino)-6-o-tolyl-pyrido[2,3-d]pyrimidine-7-carboxylic acid (2-methylamino-ethyl)-amide | (400MHz, CDCl3): 9.17(s and br s, 2H); 8.72(br s, 1H); 8.16(br s, 1H); 8.01(s, 1H); 7.88(br s, 2H); 7.38-7.23(m, 4H); 7.16(d, 1H); 6.95(d, 1H); 3.52(m, 2H); 2.86(t, 2H); 2.52(s, 3H); 2.21(s, 3H); 2.12(s, 3H); |
| 9 | 2-(3-Methanesulfonylamino-phenylamino)-6-o-tolyl-pyrido[2,3-d]pyrimidine-7-carboxylic acid (2-methylamino-ethyl)-amide | (400MHz, CDCl3): 9.21(s, 1H); 8.84(br s, 1H); 8.22(br s, 1H); 8.02(s, 1H); 7.81(br s, 1H); 7.43-7.10(m, 7H); 6.96(d, 1H); 3.51(m, 2H); 3.07(s, 3H); 2.88(br t, 2H); 2.56(s, 3H); 2.11(s, 3H); |
| 10 | 2-(4-Morpholin-4-yl-phenylamino)-6-o-tolyl-pyrido[2,3-d]pyrimidine-7-carboxylic acid (2-methylamino-ethyl)-amide | (400MHz, CDCl3): 9.01(s, 1H); 8.18(br t, 1H); 7.81(s, 1H); 7.78(br s, 1H); 7.69(br s, 2H); 7.21-7.10(m, 3H); 7.03(d, 1H); 6.86(d, 2H); 3.76(m, 4H); 3.36(m, 2H); 3.05(m, 4H); 2.67(t, 2H); 2.31(s, 3H); 1.99(s, 3H); |
| 11 | 2-(4-Morpholin-4-yl-phenylamino)-6-(2-trifluoromethyl-phenyl)-pyrido[2,3-d]pyrimidine-7-carboxylic acid (2-methanesulfonylamino-ethyl)-amide | (400MHz, DMSO-d6) 10.16(s, 1H); 9.39(s, 1H); 8.88(br t, 1H); 8.26(s, 1H); 7.86(br d, 2H); 7.79(d, 1H); 7.67(t, 1H); 7.61(t, 1H); 7.40(d, 1H); 7.10(br t, 1H); 6.99(d, 2H); 3.77(t, 4H); 3.29(m); 3.10(t, 4H); 3.01(m, 2H); 2.89(s, 3H); |
| 12 | 2-(3-Acetylamino-phenylamino)-6-(2-trifluoromethyl-phenyl)-pyrido[2,3-d]pyrimidine-7-carboxylic acid (2-methanesulfonylamino-ethyl)-amide | (400MHz, DMSO-d6) 10.35(s, 1H); 9.98(s, 1H); 9.46(s, 1H); 8.88(br t, 1H); 8.32(s, 1H); 7.92(s, 1H); 7.85-7.78(m, 2H); 7.68(t, 1H); 7.62(t, 1H); 7.43-7.36(m, 2H); 7.30(t, 1H); 7.09(br t, 1H); 3.30(m); 3.01(m, 2H); 2.89(s, 3H); 2.07(s, 3H); |
| 13 | 2-(3-Methanesulfonylamino-phenylamino)-6-(2-trifluoromethyl-phenyl)-pyrido[2,3-d]pyrimidine-7-carboxylic acid (2-methanesulfonylamino-ethyl)-amide | (400MHz, DMSO-d6) 10.41(s, 1H); 9.82(s, 1H); 9.48(s, 1H); 8.85(br t, 1H); 8.33(s, 1H); 7.93(s, 1H); 7.80(d, 1H); 7.69(m, 2H); 7.62(t, 1H); 7.41(d, 1H); 7.35(t, 1H); 7.09(br t, 1H); 6.93(d, 1H); 3.27(m); 3.09(s, 3H); 3.00(m, 2H); 2.89(s, 3H); |
| 14 | (R)-2-(4-Morpholin-4-yl-phenylamino)-6-(2-trifluoromethyl-phenyl)-pyrido[2,3-d]pyrimidine-7-carboxylic acid (pyrrolidin-2-ylmethyl)-amide | (400MHz, DMSO-d6) 10.16(s, 1H); 9.39(s, 1H); 8.66(br s, 1H); 8.25(s, 1H); 7.86(br d, 2H); 7.79(d, 1H); 7.67(t, 1H); 7.60(t, 1H); 7.41(d, 1H); 6.99(d, 2H); 3.77(t, 4H); 3.10(m, 7H); 2.78-2.67(m, 2H); 1.75-1.45(m, 4H); |
| 15 | (R)-2-(3-Acetylamino-phenylamino)-6-(2-trifluoromethyl-phenyl)-pyrido[2,3-d]pyrimidine-7-carboxylic acid (pyrrolidin-2-ylmethyl)-amide | (400MHz, DMSO-d6) 10.35(s, 1H); 10.01(s, 1H); 9.46(s, 1H); 8.65(br s, 1H); 8.31(s, 1H); 7.99(s, 1H); 7.80(m, 2H); 7.69(t, 1H); 7.61(t, 1H); 7.42(d, 1H); 7.38(d, 1H); 7.30(t, 1H); 3.20-2.97(m, 3H); 2.81-2.65(m, 2H); 2.07(s, 3H); 1.75-1.48(m, 4H); |
| 16 | (R)-2-(3-Methanesulfonylamino-phenylamino)-6-(2-trifluoromethyl-phenyl)-pyrido[2,3-d]pyrimidine-7-carboxylic acid (pyrrolidin-2-ylmethyl)-amide | (400MHz, DMSO-d6) 10.41(s, 1H); 9.46(s, 1H); 8.69(br s, 1H); 8.33(s, 1H); 7.86(s, 1H); 7.80(m, 1H); 7.69(t, 1H); 7.61(t, 1H); 7.42(d, 1H); 7.34(t, 1H); 6.91(d, 1H); 3.20-3.05(m, 6H); 2.85-2.70(m, 2H); 1.80-1.50(m, 4H); |
| 17 | (R)-2-(4,4-Dioxo-3,4-dihydro-2H-4lambda*6*-benzo[1,4]oxathiin-6-ylamino)-6- | (400MHz, DMSO-d6) 10.53(s, 1H); 9.49(s, 1H); 8.70(br s, 1H); 8.42(s, 1H); 8.34(s, 1H); 8.19(m, |

-continued

| Example-No. | Systematic Name | ¹H-NMR |
|---|---|---|
| | (2-trifluoromethyl-phenyl)-pyrido[2,3-d]pyrimidine-7-carboxylic acid (pyrrolidin-2-ylmethyl)-amide | 1H); 7.81 (d, 1H); 7.69(t, 1H); 7.62(t, 1H); 7.42(d, 1H); 7.16(d, 1H); 4.77(br s, 2H); 3.86(br s, 2H); 3.20-2.99(m, 3H); 2.87-2.65(m, 2H); 1.75-1.48(m, 4H); |

LIST OF REFERENCES

Bastin, R. J., et al., Organic Proc. Res. Dev. 4 (2000) 427-435
Biscardi, J. S., et al., Adv. Cancer Res. 76 (2000) 61-119
Merrifield, Fed. Proc. Fed. Amer. Soc. Exp. Biol. 21 (1962) 412
Stahl, P. H., and Wermuth, G., (editors), Handbook of Pharmaceutical Salts, Verlag Helvetica Chimica Acta (VHCA), Zürich (2002)
Susva, M., et al., Trends Pharmacol. Sci. 21 (2000) 489-495
WO 03/000011
WO 02/090360
WO 04/41823
WO 96/15128

The invention claimed is:

1. A compound of formula I

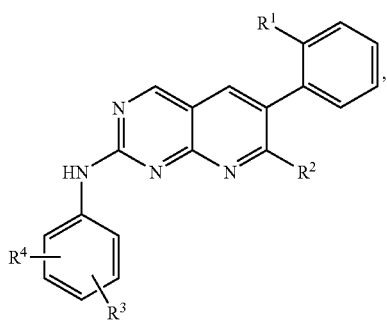

formula I wherein
R¹ is —CF$_3$;
R² is —C(O)—NH-alkyl or —C(O)—N(alkyl)$_2$, all alkyl groups being optionally substituted with —OH; —NH(alkyl);—N(alkyl)$_2$;-heterocyclyl; or —NH—S(O)$_2$-alkyl;
R³ is heterocyclyl;
   —NH—C(O)-alkyl; or
   —NH—S(O)$_2$-alkyl; and
R⁴ is hydrogen; or alternatively
R³ and R⁴ are adjacent and together with the phenyl ring to which they are attached form a 4,4-Dioxo-3,4-dihydro-2H-4lambda*6*-benzo[1,4]oxathiin-6-yl moiety;
or a pharmaceutically acceptable salt thereof.

2. A compound according to claim 1, selected from the group consisting of:
   2-(4-Morpholin-4-yl-phenylamino)-6-(2-trifluoromethyl-phenyl)-pyrido[2,3-d]pyrimidine-7-carboxylic acid (pyrrolidin-2-ylmethyl)-amide;
   2-(3-Acetylamino-phenylamino)-6-(2-trifluoromethyl-phenyl)-pyrido[2,3-d]pyrimidine-7-carboxylic acid (pyrrolidin-2-ylmethyl)-amide;
   2-(3-Methanesulfonylamino-phenylamino)-6-(2-trifluoromethyl-phenyl)-pyrido[2,3-d]pyrimidine-7-carboxylic acid (pyrrolidin-2-ylmethyl)-amide;
   2-(4,4-Dioxo-3,4-dihydro-2H-4lambda*6*-benzo[1,4]oxathiin-6-ylamino)-6-(2-trifluoromethyl-phenyl)-pyrido[2,3-d]pyrimidine-7-carboxylic acid (pyrrolidin-2-ylmethyl)-amide;
   2-(4-Morpholin-4-yl-phenylamino)-6-(2-trifluoromethyl-phenyl)-pyrido[2,3-d]pyrimidine-7-carboxylic acid (2-methanesulfonylamino-ethyl)-amide;
   2-(3-Acetylamino-phenylamino)-6-(2-trifluoromethyl-phenyl)-pyrido[2,3-d]pyrimidine-7-carboxylic acid (2-methanesulfonylamino-ethyl)-amide;
   2-(3-Methanesulfonylamino-phenylamino)-6-(2-trifluoromethyl-phenyl)-pyrido[2,3-d]pyrimidine-7-carboxylic acid (2-methanesulfonylamino-ethyl)-amide; and
   2-(4,4-Dioxo-3,4-dihydro-2H-4lambda*6*-benzo[1,4]oxathiin-6-ylamino)-6-(2-trifluoromethyl-phenyl)-pyrido[2,3-d]pyrimidine-7-carboxylic acid (2-methanesulfonylamino-ethyl)-amide.

* * * * *